(12) United States Patent
Sillevis Smitt et al.

(10) Patent No.: US 9,097,716 B2
(45) Date of Patent: Aug. 4, 2015

(54) ASSAY FOR ANTI-TR ANTIBODIES

(75) Inventors: Petrus Abraham Elisa Sillevis Smitt, Rotterdam (NL); Esther De Graaff, Rotterdam (NL)

(73) Assignee: Erasmus University Medical Center (NL)

( * ) Notice: Subject to any disclaimer, the term of this patent is extended or adjusted under 35 U.S.C. 154(b) by 0 days.

(21) Appl. No.: 14/382,007

(22) PCT Filed: Mar. 1, 2012

(86) PCT No.: PCT/NL2012/050126
§ 371 (c)(1),
(2), (4) Date: Oct. 22, 2014

(87) PCT Pub. No.: WO2013/129913
PCT Pub. Date: Sep. 6, 2013

(65) Prior Publication Data
US 2015/0050668 A1    Feb. 19, 2015

(51) Int. Cl.
*G01N 33/53* (2006.01)
*G01N 33/574* (2006.01)
*G01N 33/564* (2006.01)
*G01N 33/78* (2006.01)

(52) U.S. Cl.
CPC ........ *G01N 33/57407* (2013.01); *G01N 33/564* (2013.01); *G01N 33/78* (2013.01)

(58) Field of Classification Search
None
See application file for complete search history.

(56) References Cited

U.S. PATENT DOCUMENTS 5,420,016 A * 5/1995 Boguslaski et al. ............ 435/12

OTHER PUBLICATIONS

De Graaff et al., Identifiying the anti-TR antigen in paraneoplastic cerebellar degeneration, Molecular Biology of the Cell, (Dec. 15, 2011) vol. 22, No. 24, Abstract, p. 741.*
Written Opinion of the International Searching Authority, PCT/NL2012/050126, mailed Jul. 11, 2012, 4 pages.
Bernal et al. Anti-Tr antibodies as markers of paraneoplastic cerebellar degeneration and Hodgkin's disease. Neurology 60 (2003) 230-234.
de Graaff et al. Identification of Delta/Notch-like Epidermal Growth Factor-Related Receptor as the Tr Antigen in Paraneoplastic Cerebellar Degeneration. Ann. Neurol. 71 (2012) 815-824, Mar. 21, 2012.
Sun et al. *DNER*, an Epigenetically Modulated Gene, Regulates Glioblastoma-Derived Neurosphere Cell Differentiation and Tumor Propagation. Stem Cells 27 (2009) 1473-1486.

* cited by examiner

*Primary Examiner* — Gary W Counts
(74) *Attorney, Agent, or Firm* — Thompson Hine LLP

(57) ABSTRACT

The present invention relates to a method for determining the presence of anti-Tr antibodies in a subject comprising the steps of obtaining a sample from said subject testing the presence of said antibodies in said sample by addition of DNER protein or an antigenic part thereof and checking whether said DNER protein is bound by any antibodies in said sample Such an assay is useful for the diagnosis of paraneoplastic cerebellar degeneration that is associated with Hodgkin lymphoma, or, more generally, to type patients suffering from cerebellar ataxia. Also comprised in the invention is a kit for performing such an assay.

12 Claims, 9 Drawing Sheets

|  | 1-134 | 128-308 | 302-675 | Δ128-304 | 617-737 | 128-308 ΔG1-4 |
|---|---|---|---|---|---|---|
| Tr1 | - | + | - | - | - | - |
| Tr2 | - | + | - | - | - | - |
| Tr3 | - | + | - | - | - | - |
| Tr4 | - | + | + | + | - | - |
| Tr5 | - | + | + | + | - | +/- |
| Tr6 | - | + | - | - | - | - |
| Tr7 | - | + | + | + | - | - |
| Tr8 | - | + | + | + | - | +/- |
| Tr9 | - | + | - | - | - | - |
| Tr10 | - | + | + | + | - | - |
| Tr11 | nd | + | - | - | - | - |
| Tr12 | nd | + | nd | - | nd | - |
| HL | - | + | + | + | nd | nd |
Fig. 4B
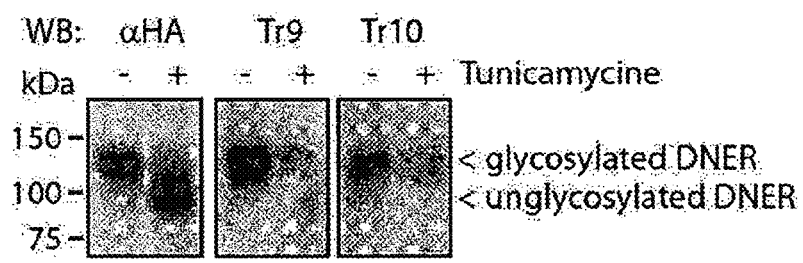
Fig. 4C
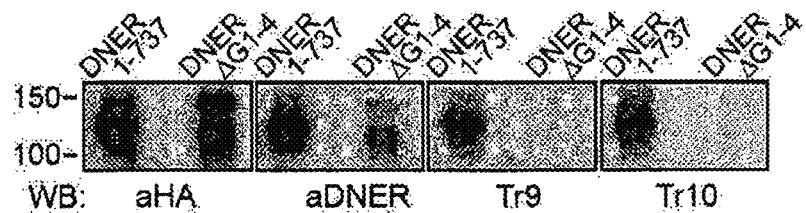
Fig. 4D

Fig. 5

```
           10         20         30         40         50         60
   MQPRRAQAPG AQLLPALALL LLLLGAGPRG SSLANPVPAA PLSAPGPCAA QPCRNGGVCT 70         80         90        100        110        120
   SRPEPDPQHP APAGEPGYSC TCPAGISGAN CQLVADPCAS NPCHHGNCSS SSSSSSDGYL 130        140        150        160        170        180
   CICNEGYEGP NCEQALPSLP ATGWTESMAP RQLQPVPATQ EPDKILPRSQ ATVTLPTWQP 190        200        210        220        230        240
   KTGQKVVEMK WDQVEVIPDI ACGNASSNSS AGGRLVSFEV PQNTSVKIRQ DATASLILLW 250        260        270        280        290        300
   KVTATGFQQC SLIDGRSVTP LQASGGLVLL EEMLALGNNH FIGFVNDSVT KSIVALRLTL 310        320        330        340        350        360
   VVKVSTCVPG ESHANDLECS GKGKCTTKPS EATFSCTCEE QYVGTFCEEY DACQRKPCQN 370        380        390        400        410        420
   NASCIDANEK QDGSNFTCVC LPGYTGELCQ SKIDYCILDP CRNGATCISS LSGFTCQCPE 430        440        450        460        470        480
   GYFGSACEEK VDPCASSPCQ NNGTCYVDGV HFTCNCSPGF TGPTCAQLID FCALSPCAHG 490        500        510        520        530        540
   TCRSVGTSYK CLCDPGYHGL YCEEEYNECL SAPCLNAATC RDLVNGYECV CLAEYKGTHC 550        560        570        580        590        600
   ELYKDPCANV SCLNGATCDS DGLNGTCICA PGFTGEECDI DINECDSNPC HHGGSCLDQP 610        620        630        640        650        660
   NGYNCHCPHG WVGANCEIHL QWKSGHMAES LTNMPRHSLY IIIGALCVAF ILMLIILIVG 670        680        690        700        710        720
   ICRISRIEYQ GSSRPAYEEF YNCRSIDSEF SNAIASIRHA RFGKKSRPAM YDVSPIAYED

730
   YSPDDKPLVT LIKTKDL
```

_US 9,097,716 B2_

SEQUENCE LISTING

<160> NUMBER OF SEQ ID NOS: 24

<210> SEQ ID NO 1
<211> LENGTH: 18
<212> TYPE: DNA
<213> ORGANISM: Artificial
<220> FEATURE:
<223> OTHER INFORMATION: primer

<400> SEQUENCE: 1
ccagtgtgct ggaattcg                                                 18

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
ctggtcgaca aatcttttgt tttaatcag                                     29

<210> SEQ ID NO 3
<211> LENGTH: 41
<212> TYPE: DNA
<213> ORGANISM: Artificial
<220> FEATURE:
<223> OTHER INFORMATION: primer

<400> SEQUENCE: 3
cggctatgaa ggtcttaact gtgctagcaa ctgtgttccg g                41

<210> SEQ ID NO 4
<211> LENGTH: 41
<212> TYPE: DNA
<213> ORGANISM: Artificial
<220> FEATURE:
<223> OTHER INFORMATION: primer

<400> SEQUENCE: 4
ccggaacaca gttgctagca cagttaagac cttcatagcc g                41

<210> SEQ ID NO 5
<211> LENGTH: 30
<212> TYPE: DNA
<213> ORGANISM: Artificial
<220> FEATURE:
<223> OTHER INFORMATION: primer

<400> SEQUENCE: 5
ctggtcgacc aaatcttttg ttttaatcag                             30

<210> SEQ ID NO 6
<211> LENGTH: 30
<212> TYPE: DNA
<213> ORGANISM: Artificial
<220> FEATURE:
<223> OTHER INFORMATION: primer

<400> SEQUENCE: 6
ctggtcgact ggttgttcac agttaagacc                             30

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
cctgaattcg gtcttaactg tgaacaacc                              29

<210> SEQ ID NO 8
<211> LENGTH: 27
<212> TYPE: DNA
<213> ORGANISM: Artificial
<220> FEATURE:
<223> OTHER INFORMATION: primer

<400> SEQUENCE: 8
caggtcgacg gaacacagtt gctagcc                                27

<210> SEQ ID NO 9
<211> LENGTH: 27
<212> TYPE: DNA
<213> ORGANISM: Artificial
<220> FEATURE:
<223> OTHER INFORMATION: primer

<400> SEQUENCE: 9
caggaattcg ctagcaactg tgttccg                                27

<210> SEQ ID NO 10
<211> LENGTH: 27
<212> TYPE: DNA
<213> ORGANISM: Artificial

```
<220> FEATURE:
<223> OTHER INFORMATION: primer

<400> SEQUENCE: 10
gcagtcgact atggccggga ggagccc                                          27

<210> SEQ ID NO 11
<211> LENGTH: 39
<212> TYPE: DNA
<213> ORGANISM: Artificial
<220> FEATURE:
<223> OTHER INFORMATION: primer

<400> SEQUENCE: 11
gatgttgcct gtggggctgc tagctccaac aactctgcg                             39

<210> SEQ ID NO 12
<211> LENGTH: 39
<212> TYPE: DNA
<213> ORGANISM: Artificial
<220> FEATURE:
<223> OTHER INFORMATION: primer

<400> SEQUENCE: 12
cgcagagttg ttggagctag cagccccaca ggcaacatc                             39

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
gccagttccg ccaactctgc gggtgg                                           26

<210> SEQ ID NO 14
<211> LENGTH: 26
<212> TYPE: DNA
<213> ORGANISM: Artificial
<220> FEATURE:
<223> OTHER INFORMATION: primer

<400> SEQUENCE: 14
ccacccgcag agttggcgga actggc                                           26

<210> SEQ ID NO 15
<211> LENGTH: 37
<212> TYPE: DNA
<213> ORGANISM: Artificial
<220> FEATURE:
<223> OTHER INFORMATION: primer

<400> SEQUENCE: 15
gaagtgccac aggccactag tgtaaagatt cggcagg                               37

<210> SEQ ID NO 16
<211> LENGTH: 37
<212> TYPE: DNA
<213> ORGANISM: Artificial
<220> FEATURE:
<223> OTHER INFORMATION: primer

<400> SEQUENCE: 16
cctgccgaat ctttacacta gtggcctgtg gcacttc                               37
```

```
<210> SEQ ID NO 17
<211> LENGTH: 30
<212> TYPE: DNA
<213> ORGANISM: Artificial
<220> FEATURE:
<223> OTHER INFORMATION: primer

<400> SEQUENCE: 17
cttcattggt tttgtggctg actctgttgc                                        30

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
gcaacagagt cagccacaaa accaatgaag                                        30

<210> SEQ ID NO 19
<211> LENGTH: 20
<212> TYPE: PRT
<213> ORGANISM: Artificial
<220> FEATURE:
<223> OTHER INFORMATION: linker

<400> SEQUENCE: 19

Ala Ser Gly Leu Asn Asp Ile Phe Glu Ala Gln Lys Ile Glu Trp His
1               5                   10                  15

Glu Gly Gly Gly
            20

<210> SEQ ID NO 20
<211> LENGTH: 28
<212> TYPE: PRT
<213> ORGANISM: Artificial
<220> FEATURE:
<223> OTHER INFORMATION: signal peptide

<400> SEQUENCE: 20

Met Asn Phe Ile Pro Val Asp Ile Pro Leu Leu Met Ile Phe Leu Val
1               5                   10                  15

Thr Thr Gly Gly Ser Ala Leu Glu Lys Leu Ala Thr
            20                  25

<210> SEQ ID NO 21
<211> LENGTH: 11
<212> TYPE: PRT
<213> ORGANISM: Artificial
<220> FEATURE:
<223> OTHER INFORMATION: myc-tag

<400> SEQUENCE: 21

Met Glu Gly Lys Leu Ile Ser Glu Glu Asp Leu
1               5                   10

<210> SEQ ID NO 22
<211> LENGTH: 19
<212> TYPE: DNA
<213> ORGANISM: Artificial
<220> FEATURE:
<223> OTHER INFORMATION: shRNA#1

<400> SEQUENCE: 22
```
aaacccttgg tcacactga                                                              19

<210> SEQ ID NO 23
<211> LENGTH: 19
<212> TYPE: DNA
<213> ORGANISM: Artificial
<220> FEATURE:
<223> OTHER INFORMATION: shRNA#2

<400> SEQUENCE: 23
gattctgttg ctaagtcca                                                              19

<210> SEQ ID NO 24
<211> LENGTH: 737
<212> TYPE: PRT
<213> ORGANISM: Homo sapiens

<400> SEQUENCE: 24

```
Met Gln Pro Arg Arg Ala Gln Ala Pro Gly Ala Gln Leu Leu Pro Ala
1               5                   10                  15

Leu Ala Leu Leu Leu Leu Leu Leu Gly Ala Gly Pro Arg Gly Ser Ser
            20                  25                  30

Leu Ala Asn Pro Val Pro Ala Ala Pro Leu Ser Ala Pro Gly Pro Cys
        35                  40                  45

Ala Ala Gln Pro Cys Arg Asn Gly Gly Val Cys Thr Ser Arg Pro Glu
    50                  55                  60

Pro Asp Pro Gln His Pro Ala Pro Ala Gly Glu Pro Gly Tyr Ser Cys
65                  70                  75                  80

Thr Cys Pro Ala Gly Ile Ser Gly Ala Asn Cys Gln Leu Val Ala Asp
                85                  90                  95

Pro Cys Ala Ser Asn Pro Cys His His Gly Asn Cys Ser Ser Ser Ser
            100                 105                 110

Ser Ser Ser Ser Asp Gly Tyr Leu Cys Ile Cys Asn Glu Gly Tyr Glu
        115                 120                 125

Gly Pro Asn Cys Glu Gln Ala Leu Pro Ser Leu Pro Ala Thr Gly Trp
    130                 135                 140

Thr Glu Ser Met Ala Pro Arg Gln Leu Gln Pro Val Pro Ala Thr Gln
145                 150                 155                 160

Glu Pro Asp Lys Ile Leu Pro Arg Ser Gln Ala Thr Val Thr Leu Pro
                165                 170                 175

Thr Trp Gln Pro Lys Thr Gly Gln Lys Val Val Glu Met Lys Trp Asp
            180                 185                 190

Gln Val Glu Val Ile Pro Asp Ile Ala Cys Gly Asn Ala Ser Ser Asn
        195                 200                 205

Ser Ser Ala Gly Gly Arg Leu Val Ser Phe Glu Val Pro Gln Asn Thr
    210                 215                 220

Ser Val Lys Ile Arg Gln Asp Ala Thr Ala Ser Leu Ile Leu Leu Trp
225                 230                 235                 240

Lys Val Thr Ala Thr Gly Phe Gln Gln Cys Ser Leu Ile Asp Gly Arg
                245                 250                 255

Ser Val Thr Pro Leu Gln Ala Ser Gly Gly Leu Val Leu Glu Glu
            260                 265                 270
```

```
Met Leu Ala Leu Gly Asn Asn His Phe Ile Gly Phe Val Asn Asp Ser
            275                 280                 285

Val Thr Lys Ser Ile Val Ala Leu Arg Leu Thr Leu Val Val Lys Val
        290                 295                 300

Ser Thr Cys Val Pro Gly Glu Ser His Ala Asn Asp Leu Glu Cys Ser
305                 310                 315                 320

Gly Lys Gly Lys Cys Thr Thr Lys Pro Ser Glu Ala Thr Phe Ser Cys
                325                 330                 335

Thr Cys Glu Glu Gln Tyr Val Gly Thr Phe Cys Glu Glu Tyr Asp Ala
            340                 345                 350

Cys Gln Arg Lys Pro Cys Gln Asn Asn Ala Ser Cys Ile Asp Ala Asn
        355                 360                 365

Glu Lys Gln Asp Gly Ser Asn Phe Thr Cys Val Cys Leu Pro Gly Tyr
    370                 375                 380

Thr Gly Glu Leu Cys Gln Ser Lys Ile Asp Tyr Cys Ile Leu Asp Pro
385                 390                 395                 400

Cys Arg Asn Gly Ala Thr Cys Ile Ser Ser Leu Ser Gly Phe Thr Cys
                405                 410                 415

Gln Cys Pro Glu Gly Tyr Phe Gly Ser Ala Cys Glu Glu Lys Val Asp
            420                 425                 430

Pro Cys Ala Ser Ser Pro Cys Gln Asn Asn Gly Thr Cys Tyr Val Asp
        435                 440                 445

Gly Val His Phe Thr Cys Asn Cys Ser Pro Gly Phe Thr Gly Pro Thr
    450                 455                 460

Cys Ala Gln Leu Ile Asp Phe Cys Ala Leu Ser Pro Cys Ala His Gly
465                 470                 475                 480

Thr Cys Arg Ser Val Gly Thr Ser Tyr Lys Cys Leu Cys Asp Pro Gly
                485                 490                 495

Tyr His Gly Leu Tyr Cys Glu Glu Tyr Asn Glu Cys Leu Ser Ala
            500                 505                 510

Pro Cys Leu Asn Ala Ala Thr Cys Arg Asp Leu Val Asn Gly Tyr Glu
        515                 520                 525

Cys Val Cys Leu Ala Glu Tyr Lys Gly Thr His Cys Glu Leu Tyr Lys
    530                 535                 540

Asp Pro Cys Ala Asn Val Ser Cys Leu Asn Gly Ala Thr Cys Asp Ser
545                 550                 555                 560

Asp Gly Leu Asn Gly Thr Cys Ile Cys Ala Pro Gly Phe Thr Gly Glu
                565                 570                 575

Glu Cys Asp Ile Asp Ile Asn Glu Cys Asp Ser Asn Pro Cys His His
            580                 585                 590

Gly Gly Ser Cys Leu Asp Gln Pro Asn Gly Tyr Asn Cys His Cys Pro
        595                 600                 605

His Gly Trp Val Gly Ala Asn Cys Glu Ile His Leu Gln Trp Lys Ser
    610                 615                 620

Gly His Met Ala Glu Ser Leu Thr Asn Met Pro Arg His Ser Leu Tyr
625                 630                 635                 640

Ile Ile Ile Gly Ala Leu Cys Val Ala Phe Ile Leu Met Leu Ile Ile
                645                 650                 655

Leu Ile Val Gly Ile Cys Arg Ile Ser Arg Ile Glu Tyr Gln Gly Ser
            660                 665                 670

Ser Arg Pro Ala Tyr Glu Glu Phe Tyr Asn Cys Arg Ser Ile Asp Ser
        675                 680                 685

Glu Phe Ser Asn Ala Ile Ala Ser Ile Arg His Ala Arg Phe Gly Lys
```

-continued

```
                690                 695                 700
Lys Ser Arg Pro Ala Met Tyr Asp Val Ser Pro Ile Ala Tyr Glu Asp
705                 710                 715                 720

Tyr Ser Pro Asp Asp Lys Pro Leu Val Thr Leu Ile Lys Thr Lys Asp
                725                 730                 735
Leu
```

ASSAY FOR ANTI-TR ANTIBODIES

FIELD OF THE INVENTION

The invention relates to the field of immunoassays, more particularly to the filed of assays in neurological diseases, more specifically with relation to paraneoplastic cerebellar degeneration.

INTRODUCTION

Paraneoplastic cerebellar degeneration (PCD) is a heterogenous group of neurological disorders characterized by subacute cerebellar ataxia which coincides with the presence of specific tumour types and antineural antibodies.

The clinical cerebellar ataxia symptoms that are evident in patients with PCD are caused by Purkinje neuronal loss or by loss of function of Purkinje neuronal cells in the cerebellum; it is manifested by dysarthria, limb and gait ataxia, and nystagmus. Radiologic imaging occasionally reveals cerebellar atrophy.

As is the case with other paraneoplastic syndromes, PCD is believed to be due to an autoimmune reaction targeted against components of the central nervous system (in PCD, this is specifically Purkinje cells). It is thought to be triggered when tumor cells (in PCD, most commonly ovarian or breast cancer) express a protein normally expressed in the brain (in PCD, this is the Purkinje neuronal protein termed cdr2). This is believed to trigger an anti-tumor immune response that may be clinically significant, but also an anti-neuronal immune response. Such PCD patients harbor an anti-neuronal antibody known as anti-Yo (named after the first two letters of the index patient). PCD may be associated with other tumors—when associated with small cell lung cancer, it is associated with an antibody termed "anti-Hu" (more commonly associated with paraneoplastic subacute sensory neuropathy and/or limbic encephalitis), but also further antibodies (anti-Ri, anti-Ma, anti-CV2, anti-amphiphysin) have been identified.

One particular form of PCD is associated with Hodgkin lymphoma (HL) and is characterized by the presence of anti-Tr antibodies. These antibodies recognize a specific punctuate immunoreactivity in the large dendritic tree as well as in the soma of Purkinje cells, but not in the axons. Although the disease itself was recognised already long ago (Horwich, L. et al., 1966, J. Neurol. Neurosurg. Psychiatry 29:45-51), the detection of the anti-Tr antibodies in 1997 (Graus, F. et al., 1997, J. Neuroimmunol. 74:55-61) showed that these were associated with the syndrome. Since then, it has been searched for the antigen to which these antibodies are directed. However, until now such an antigen, despite all the research involved, has not been identified.

Diagnosis of this particular form of Hodgkin lymphoma associated PCD is seriously hampered by the fact that no antigen is available. Now, only an indirect method to show the presence of the anti-Tr antibody is used. Such a test is currently offered commercially (e.g. by Immco Diagnostics). The characteristic punctuate staining of anti-Tr sera is only one prerequisite of the diagnosis: the diagnosis is usually confirmed by performing antigen blocking experiments (Shams'ili S. et al., 2003, Brain 126:1409-1418; Bernal, F. et al., 2003, Neurology 53:1719-1723). For this, cerebellar sections are first pre-incubated with undiluted anti-Tr sera that require testing and subsequently incubated with diluted biotinylated standard anti-Tr serum. This method, by definition, is less reliable than detection by an assay with the antigen itself. Thus, there is ample need for identification of the antigen and incorporating this into an assay for the detection of the presence of the anti-Tr antibody and, because of that, diagnosis of the presence of HL-associated PCD.

SUMMARY OF THE INVENTION

The current inventors have been able to identify the antigen that is capable of binding to the anti-Tr auto-antibody.

The invention therefore comprises a method for determining the presence of anti-Tr antibodies in a subject comprising the steps of
  a. obtaining a sample from said subject
  b. testing the presence of said antibodies in said sample by addition of DNER protein or an antigenic part thereof and checking whether said DNER protein is bound by any antibodies in said sample.

Preferably in said method the DNER protein or antigenic part thereof is labeled. In a further preferred embodiment the sample is a blood, plasma, serum or CSF sample.

Such a method preferably entails an immunoassay, more preferably a cell-based immunoassay.

In a further preferred embodiment the method is applied to a human subject, preferably wherein the human subject is suffering from paraneoplastic cerebellar degeneration and/or ataxia.

Alternatively, the invention comprises a method for detection of Hodgkin lymphoma by performing a method according to the invention.

Further comprised in the present invention is a method for typing subjects suffering from paraneoplastic cerebellar degeneration and/or ataxia comprising performing a method according to the invention.

Also part of the invention is the use of the DNER protein or an antigenic part thereof for the detection of anti-Tr antibodies. Preferably in such a use the DNER protein or an antigenic part thereof is labeled.

Alternatively, the invention comprises the use of a cell line transfected with a construct encoding a DNER protein or antigenic part thereof for the detection of anti-Tr antibodies.

In another aspect the invention comprises a kit for performing an immunoassay wherein said kit comprises a DNER protein or antigenic part thereof and/or a cell line that is capable of producing said protein or part thereof, and an anti-Tr antibody as positive control. Preferably in such a kit the DNER protein or antigenic part thereof is labeled.

BRIEF DESCRIPTION OF THE DRAWINGS

FIGS. 4A-E show Tr epitope mapping of DNER.

FIG. 5 shows DNER sequence (SEQ. ID NO. 24).

FIG. 1. IDENTIFICATION OF DNER AS THE TR ANTIGEN

A) Coomassie stained gel of total rat brain extracts immunoprecipitated with anti-Tr positive sera and used for mass spectrometry analysis.

B) HeLa cells expressing HA-DNER (green) are positively stained by two anti-Tr sera (Tr9 and Tr6, 1:200, red), CSF of the same patient (Tr6, 1:100, red) but not by the control sera (ctrl, 1:200, red). The merged images reveal non-transfected cells by DAPI staining. Scale bar: 10 μm.

C) Western blot analysis of total HEK293T cell extracts expressing HA-DNER (input) and purified HA-DNER (HA-DNER). Untransfected HEK293T cells (mock) are used as control. HA-DNER was purified by immunoprecipitation using anti-HA antibodies. The asterisk's denote background bands also present in untransfected HEK293T cells.

D) Representative images of hippocampal neurons (days in vitro 11) stained with anti-DNER (green) and anti-Tr serum Tr9 (red). Zoom indicates punctuate DNER staining in neurites that strongly co-localize with anti-Tr serum. Scale bar: 20 μm.

Figure 2:
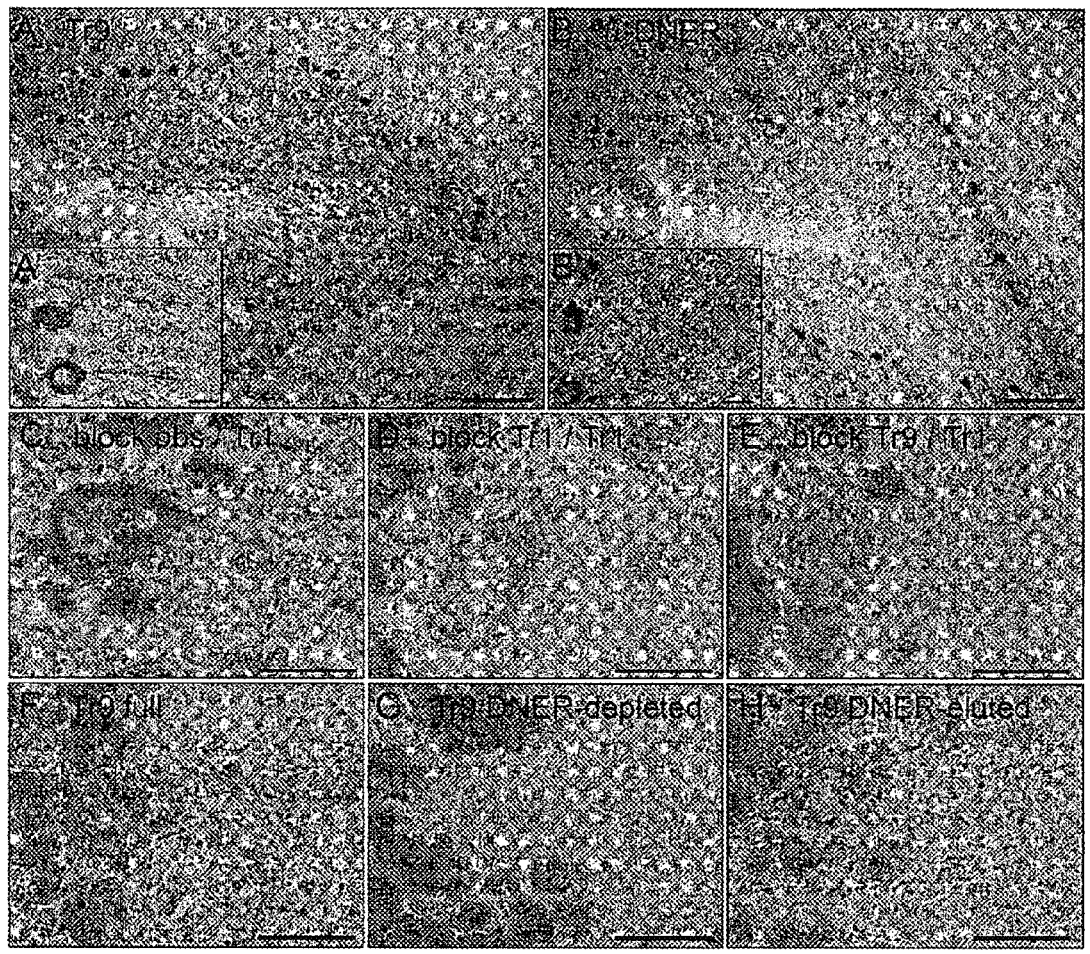
FIGS. 2A-H show immunohistochemistry of anti-DNER and anti-Tr sera on rat cerebella.

FIG. 2. IMMUNOHISTOCHEMISTRY OF ANTI-DNER AND ANTI-TR SERA ON RAT CEREBELLA (A-B) Sagittal section of rat brain stained with serum of a patient known to contain the anti-Tr antibodies (A) or commercial anti-DNER (B). A'-B': Higher magnification shows that anti-DNER antibodies lead to the identical dot-like somatodendritic staining as described for anti-Tr sera.

(C-E) Standard blocking procedure currently used to test for presence of anti-Tr antibodies in sera. (C) Punctate staining after incubation with standard biotinylated serum. (D-E) Staining disappears when previously incubated with unbiotinylated serum from the same patient (D) or serum from another patient (E).

(F-H) Depletion of anti-DNER antibodies from anti-Tr positive sera (F) obliterates the anti-Tr staining pattern (G). The eluted fraction, containing purified anti-DNER antibodies, retains the normal punctuate staining (H). Note that a lower dilution was used in F-H (1/20.000) than in B-E (1/400). Scale bar: 200 μm in A, B and 25 μm in A'-B', C-D, F-H.

FIG. 3. KNOCK DOWN OF DNER ABOLISHES TR REACTIVITY IN HIPPOCAMPAL NEURONS

A) In neurons transfected with a control construct, normal DNER (green) and Tr (red) reactivity is observed (upper panel). In all neurons transfected with shRNA constructs expressing shRNA against DNER and β-Galactosidase (blue) both DNER expression and Tr reactivity is lacking (lower panel). Scale bar: 20 μm. B) Summary of DNER knock down experiments. Quantification of the number of TR and DNER positive neurons expressing control shRNA (n=162), DNER-shRNA#1 (n=133) or DNER-shRNA#2 (n=134).

FIG. 4. TR EPITOPE MAPPING OF DNER (A) The upper panel gives a schematic representation of DNER to indicate the epitope regions (numbers depict amino acid, light grey boxes indicate EGF domains, SP: N-terminal signal peptide, TM: transmembrane domain). Lower panel: Epitope mapping of DNER by expressing HA- or myc-tagged DNER deletion constructs (green) in HeLa cells stained by anti-Tr sera (red) displays two groups of patients: Tr9 detects one epitope encompassing aa 128-308 only, whereas Tr8 detects a second epitope within aa 302-675. Scale bar, 10 μm.

(B) Summary of the cell-based Tr epitope mapping experiments with the 13 different anti-Tr sera, including the Tr-positive serum from the HL patient without ataxia.

(C) Western blot analysis reveals that Tunicamycin treatment of HA-DNER expressing HEK293T cells inhibits the glycosylation of DNER as seen by the reduction in molecular weight. The anti-Tr positive sera (Tr9 and Tr5) no longer recognize unglycosylated DNER.

(D) Mutating four N-glycosylation sites in DNER1-737 abolishes the recognition by the anti-Tr sera (Tr9 and Tr10) as analyzed on Western blotting.

(E) Mutating four N-glycosylation sites in DNER128-308 completely abolishes the recognition by 9 anti-Tr sera, whereas the remaining 3 sera only gave minimal reactivity (see also B).

FIG. 5. DNER SEQUENCE

The protein has a large extracellular domain, ranging from amino acid 35-640 (the first 34 amino acids form the signal peptide). The transmembrane part only comprises 20 amino acids (641-661), while the intracellular part forms the C-terminal end of the molecule (amino acids 662-735). The extracellular domain contains 10 EGF like domains:
  EGF like 1 domain 44-92
  EGF like 2 domain 94-133
  EGF like 3 domain 309-348
  EGF like 4 domain 349-390
  EGF like 5 domain 392-428
  EGF like 6 domain 430-466
  EGF like 7 domain 468-503
  EGF like 8 domain 505-541 (potential calcium binding)
  EGF like 9 domain 543-579
  EGF like 10 domain 581-617 (potential calcium binding)
  EGF like 1 and 2 taken together are thought—on basis of sequence similarity—to interact with NOTCH1.

Glycosylation takes place on amino acid 223 and 564.

DETAILED DESCRIPTION OF THE INVENTION

In recent years, progress has been made in the identification of various antineuronal antibodies in different ways. Overlapping expression patterns led to the identification of antibodies against the metabotropic glutamate receptor 1 (mGluR1) in PCD associated with HL (Sillevis Smitt, P. et al., 2000, N. Engl. J. Med. 342:21-27) and anti-N-methyl-D-aspartate receptor (NMDAR) antibodies in limbic encephalitis (Dalmau J. et al., 2007, Ann. Neurol. 61:25-36) while association with a known complex identified Leucine-rich, glioma inactivated 1 (Lgi-1) as the antigen recognized by antibodies against voltage gated potassium channels (VGKC) (Irani, S. R. et al., 2010, Brain 133:2734-2748; Lai M., et al., 2010, Lancet Neurol. 9:776-785). Recently immunoprecipitation followed by mass spectrometry analysis (IP-MS) directed the identification of antibodies against the glutamate receptor subunits GluR1 and GluR2 (Lai M. et al., 2009, Ann. Neurol. 65:424-434), the Gamma Amino Butyric Acid B (GABAB) Receptor-1 and -2 subunits (Lancaster E. et al., 2010, Lancet Neurol. 9:67-76) and mGluR5 (Lancaster E. et al., 2011, Neurology 77:1698-1701) in limbic encephalitis. In these cases, clear bands were already visible on coomassie stained gels after immunoprecipitation. This was not the case with the anti-Tr antibodies that are associated with HL in PCD. In order to proceed we took advantage of the fact that all anti-Tr sera recognize the same epitope (FIG. 2C-E and Bernal et al 2003). This meant that we had to analyze the entire peptide data set obtained by IP-MS in order to identify proteins that were precipitated by all 4 anti-Tr sera.

In the end, however, the present inventors were able to conclude that the protein DNER (Delta/Notch-like Epidermal growth factor related Receptor) contained the epitope that caused the binding of the anti-Tr antibodies and thus is the long-sought antigen. As is shown in the experimental part, the fact that DNER is the antigen has been confirmed by histochemical evidence. This finding enables the production of a quick and reliable assay for screening for anti-Tr antibodies. We mapped the main epitope for all 13 anti-Tr sera (including the serum from a HL patient without ataxia) to an extracellular region of 176 amino acids between amino acids 128-304 of DNER. It further appeared that that Tr antigenicity is dependent on N-glycosylation of this region. Whether this is caused by recognition of the glycogen chains or due to the folding of the protein remains to be determined and has no implications on the current invention. Final proof was given by the fact that anti-Tr sera depleted of DNER-antibodies no longer displayed the typical somatodendritic punctuate staining. Although the main epitope recognized by all 12 anti-Tr positive sera from PCD patients was mapped to an extracellular 176 aa region between EGF domains 2 and 3, five of these sera could recognize a second epitope, also in the extracellular region of DNER. The clinical phenotype, known in 4 of these 5 patients, was not different from the seven other patients (Table 1). The 13th anti-Tr positive serum from the non-ataxic HL patient also detected both epitopes, identical to the five PCD patients.

The Tr antigen DNER is expressed throughout the brain during development and adulthood, but is highly expressed in the Purkinje cells in a punctuate somatodendritic manner (Eiraku, M. et al., 2002, J. Biol. Chem. 277:25400-25407; Nishizumi, H. et al., 2002, Neuroreport. 13:909-915). Similar to the subacute cerebellar ataxia observed in anti-Tr positive patients, mice lacking DNER exhibited motor discoordination in the fixed bar and rotarod tests. Moreover, the cerebellum from knockout mice showed significant retardation in morphogenesis and persistent abnormality in fissure organization (Tohgo, A. et al., 2006, Mol. Cell Neurosci. 31:326-333).

DNER protein is an epidermal growth factor (EGF)-like repeat-containing single-pass transmembrane protein that is specifically expressed in the developing and mature central nervous system. Sequence analysis shows that the 10 EGF-like repeats in the extracellular domain are closely related to those of the developmentally important receptor Notch and its ligand Delta. Accordingly the protein was named Delta/Notch-like EGF-related receptor (DNER). DNER protein is strongly expressed in several types of post-mitotic neurons, including cortical and hippocampal pyramidal neurons, cerebellar granule cells, and Purkinje cells. DNER protein is localized to the dendritic plasma membrane and endosomes and is excluded from the axons, even when overexpressed.

The identification of DNER as Tr antigen in this study simplifies the method for determining the presence of anti-Tr antibodies in patients with subacute cerebellar symptoms. Instead of using the strict immunohistochemical criteria followed by a blocking experiment (Bernal et al., supra), a simple assay based on the expression of exogenous DNER can now be used.

Accordingly, the present invention is directed to an immunoassay method for typing patients with paraneoplastic cerebellar degeneration and/or cerebellar ataxia comprising testing for the presence of anti-Tr antibodies with its antigen DNER or an antigenic part thereof. For this invention an antigenic part of the DNER protein is defined as that part of the DNER protein that is capable of binding to the anti-Tr antibody. Thus an antigenic part of the DNER protein can for example be the part between EGF-like domain 2 and 3.

In principle the test can be any sort of (immuno-)assay in which the binding between the DNER protein (or antigenic part thereof) with the anti-Tr antibody which is to be detected can be established. Preferably, to enable detection, the DNER protein or antigenic part thereof is labeled, for which labeling any suitable label can be used. Suitable labels for instance could be chosen from enzymes, dyes, radioactive moieties, specific tags that can be recognised by secondary antibodies, fluorescent proteins (e.g. GFP) etc.

For such a test a sample taken from a subject that is suspected of having PCD with HL is used, which sample is a sample from a body liquid, preferably is a blood sample (like a serum or plasma sample) or a cerebrospinal fluid (CSF) sample.

The subject preferably is a human.

Thus, the test can be a RIA (radio-immunoassay), EIA (enzyme immunoassay), an ELISA (enzyme-linked immunosorbent assay) or any other type of immunoassay and such an assay may be direct, sandwich, competitive or non-competitive or any other type of assay. The assay may involve solid supports such as beads, columns, (glass or ceramic) plates and the like and it may be conducted on micro-titer plates, reagent cups or any suitable holder.

Preferably, the assay is a cell-based assay in which the labeled antigen is (recombinantly) produced by a cell. Such a cell is preferably a mammalian and more preferably a human cell, such as a CHO cell, a HeLa cell, a HEK-293 cell, a Vero cell, a 293-T cell, a 3T3 cell, a H1299 cell, a Jurkat cell, a JY cell, or a Raji cell. Cells can be transiently or stably transfected with a construct that enables expression of the DNER protein or an antigenic part thereof. Production of such a construct that enables expression of the DNER protein or an antigenic part thereof, transfection of a cell with such a construct, culturing said cell and harvesting the cultured cells or the produced DNER protein is well within the capability of the skilled person. Further, in the experimental part a clear description is given of an example how to perform an assay as claimed.

The assay is preferably used when a subject is suspected of suffering from PCD with HL, but it can also be a part of a series of assays to type subjects suffering from PCD or cerebellar ataxia. In such a case, also assays for the detection of anti-Yo, anti-Hu, anti-Ri, anti-Ma, anti-CV2, anti-mGluR1 and/or anti-amphiphysin antibodies maybe comprised in the series of assays. The term "typing of subjects" in this application therefore means to detect which anti-neuronal antibodies (and/or which tumours) are present in the subject and are responsible for the clinical signs of PCD or cerebellar ataxia. Thus also a method for the typing of subjects using an assay according to the invention is part of the current invention.

Further part of the invention is a kit for performing the assays as described. Such a kit will comprise the DNER protein or an antigenic part thereof, and/or a cell line that can produce said protein or part thereof. Further, the kit will preferably comprise an anti-Tr antibody to be used as a positive control. Also instructions for use of the kit may be present. If the assay is used as part of a typing protocol for PCD patients, the kit may further comprise additional assay requirements for testing of anti-neuronal antibodies such as anti-Yo, anti-Hu, anti-Ri, anti-Ma, anti-CV2, anti-mGluR1 and/or anti-amphiphysin antibodies.

Experimental Part

Patients

Twelve anti-Tr positive patients were selected in our hospital. The most relevant clinical features of 11 of the 12 anti-Tr positive patients are given in Table 1. Clinical information was lacking from Tr-positive patient 5. All patients suffered subacute and severe truncal and limb ataxia with nystagmus and/or cerebellar dysarthria. Ten patients were diagnosed with HL and in all of them the cerebellar symptoms preceded the detection of HL.

Assessment of Patient's Disability

The patients' disability was assessed using a modified Rankin scale (mRS) (Keime-Guibert, F. et al., 1999, Neurology 53:1719-1723). On the mRS a score of 0 represents an asymptomatic patient; 1, symptoms that do not interfere with lifestyle; 2, symptoms that lead to some restriction of lifestyle but do not prevent totally independent existence; 3, symptoms significantly interfere with lifestyle or prevent totally independent existence; 4, symptoms clearly prevent independent existence, although the patient does not need constant attention; 5, severe disability with total dependence requiring constant attention; 6, death from neurological cause 4.

Antibodies and Expression Constructs

For immunocytochemistry, antibodies were used in the following dilutions: mouse anti-β-galactosidase (Promega, Leiden, Netherlands) 1:2,000, goat anti-DNER (R&D systems, Abingdon, United Kingdom) 1:400-1:2,000, rabbit anti-HA (Santa-CruzHeidelberg, Germany) 1:400, patients' sera: 1:50-1:20,000. Cy3-conjugated donkey anti-Human (Jackson's lab, Newmarket, UK), Alexa488- and Alexa568- conjugated secondary antibodies (Molecular Probes, Breda, Netherlands) and FITC-conjugated anti-goat (Jackson) were used in a 1:400 dilution. For Western blotting: HRP-conjugated donkey anti-human (Calbiochem, Darmstadt, Germany) 1:10,000 and HRP-conjugated swine anti-rabbit, -mouse or -goat (Dako, Heverlee, Belgium) 1:2500 were used.

Full length wild type HA-tagged mouse DNER cDNA in pDisplay was kindly provided by M. Kengaku (Kyoto) and was previously described10. DNER-GFP-bio, the deletion and glycosylation mutants were generated by PCR and cloning in pGW111.

Primers Used:

| Name | sequence (5'-3') | SEQ ID NO |
|---|---|---|
| dnerF1 | Ccagtgtgctggaattcg | 1 |
| dnerR1 | ctgGTCGACaaatcttttgttttaatcag | 2 |
| dnerΔ1F | cggctatgaaggtcttaactgtgctagcaactgtgttccgg | 3 |
| dnerΔ1R | ccggaacacagttgctagcacagttaagaccttcatagccg | 4 |
| dnerR2 | ctgGTCGACcaaatcttttgttttaatcag | 5 |
| dnerE2R | ctggtcgactggttgttcacagttaagacc | 6 |
| dnerE2F | cctgaattcggtcttaactgtgaacaacc | 7 |
| dnerE3R | caggtcgacggaacacagttgctagcc | 8 |
| dnerE3F | caggaattcgctagcaactgtgttccg | 9 |
| dnerTMR | gcagtcgactatggccgggaggagccc | 10 |
| delG1F | gatgttgcctgtgggGCtgcTagCtccaacaactctgcg | 11 |
| delG1R | cgcagagttgttggaGctAgcaGCcccacaggcaacatc | 12 |
| delG2F | gccagttccGCcaactctgcgggtgg | 13 |
| delG2R | ccacccgcagagttgGCggaactggc | 14 |
| delG3F | gaagtgccacagGCcactAGTgtaaagattcggcagg | 15 |
| delG3R | cctgccgaatctttacACTagtgGCctgtggcacttc | 16 |
| delG4F | cttcattggttttgtgGCtgactctgttgc | 17 |
| delG4R | gcaacagagtcaGCcacaaaaccaatgaag | 18 |

Constructs:

| | |
|---|---|
| HA-DNER1-737 | PCR:dnerF1/dnerR1, EcoRI-SalI into pGW1 |
| DNER GFPbio | PCR:dnerF1/dnerR2, EcoRI-SalI into pGW1-GFPbio |
| HA-DNER1-134 | PCR:dnerF1/dnerE2R, EcoRI-SalI into pGW1 |
| myc-DNER128-308 | PCR:dnerE2F/dnerE3R, EcoRI-SalI into pGW1, insert recloned into AscI-NotI GW-Spmyc |
| myc-DNER304-675 | PCR:dnerE3F/dnerTMR, EcoRI-SalI into pGW1, insert recloned into AscI-NotI pGW-Spmyc |
| HA-DNERΔ128-304 | PCRdnerF1/dnerΔ1F/dnerΔ1R/dnerR1, EcoRI-SalI into pGW1 |
| HA-DNERΔG1-4 | consecutively: delG1,2,3,4F/R&dnerF1/dnerR1, EcoRI-SalIinto pGW1 |

The template for all constructs was the HA-DNER in pDISPLAY, kindly provided by M. Kengaku₁. All DNER constructs were subcloned in pGW1 expression vectors for optimal neuronal expression₂. A linker encoding the sequence ASGLNDIFEAQKIEWHEGGG, which is the substrate of biotin ligase BirA was inserted into the AscI EcoRI sites after the GFP in pGW1-GFP₃. In pGW-SPmyc a linker encoding the signal peptide MNFIPVDIPLLMIFLVT-TGGSALEKLAT was inserted before the myc-tag MEGKLISEEDL.

Immunoprecipitation and Mass Spectrometry

Extracts were made from adult total rat brain using 1% NP40 lysis buffer (10 mM Hepes, pH 7.5, 150 mM NaCl, 1% NP40 and complete protease inhibitor (Roche). 2.5 mg protein was precleared with 50 ul protA/protG sepharose, mixed 1:1, for 1 hour at 4° C. and the supernatant was subsequently incubated overnight at 4° C. with 10 ul sera. The following morning 50 ul protA/protG (1:1) sepharose was added and left to incubate for an additional 4 hours at 4° C. The sepharose beads were washed 5 times with lysis buffer and loaded on a 4-12% Bis-Tris gel (Invitrogen, Breda, Netherlands).

Mass spectrometry was mainly performed as described before (Lansbergen, G. et al., 2006, Dev. Cell. 11:21-32; Jaworski, J. et al., 2009, Neuron. 61: 85-100). For mass spectrometry analysis, 1D SDS-PAGE gel lanes were cut into 2-mm slices using an automatic gel slicer and subjected to in gel reduction with dithiothreitol, alkylation with iodoacetamide and digestion with trypsin (sequencing grade, Promega, Leiden, Netherlands), essentially as described previously (Wilm, M. et al., 1996, Nature 379:466-469). Nanoflow LCMS/MS was performed on an 1100 series capillary LC system (Agilent Technologies, Amstelveen, Netherlands) coupled to an LTQ linear ion trap mass spectrometer (Thermo, Breda, Netherlands) operating in positive mode and equipped with a nanospray source. Peptide mixtures were trapped on a ReproSil C18 reversed phase column (column dimensions 1.5 cm×100 μm, packed in-house; Dr Maisch GmbH, Ammerbuch-Entringen, Germany) at a flow rate of 8 μl/min. Peptide separation was performed on ReproSil C18 reversed phase column (column dimensions 15 cm×50 μm, packed inhouse; Dr Maisch GmbH, Ammerbuch-Entringen, Germany) using a linear gradient from 0 to 80% B (A=0.1 M acetic acid; B=80% (v/v) acetonitrile, 0.1 M acetic acid) in 70 min and at a constant flow rate of 200 nl/min using a splitter. The column eluent was directly sprayed into the ESI source of the mass spectrometer. Mass spectra were acquired in continuum mode; fragmentation of the 4 peptides was performed in data-dependent mode. Peak lists were automatically created from raw data files using the Mascot Distiller software (version 2.1; MatrixScience, London, UK). The Mascot search algorithm (version 2.2) was used for searching against the International Protein Index database (release number IPI_rat_20091106.fasta). The peptide tolerance was typically set to 2 Da and the fragment ion tolerance to 0.8 Da. A maximum number of 2 missed cleavages by trypsin were allowed and carbamidomethylated cysteine and oxidized methionine were set as fixed and variable modifications, respectively. The Mascot score cut-off value for a positive protein hit was set to 31. Proteins present in the anti-Hu serum were omitted from the individual lists obtained by immunoprecipitation with the 4 anti-Tr positive sera. The remaining proteins of the 4 lists were compared by hand, leading to 12 proteins identified in all 4 anti-Tr immunoprecipitations. These were all further checked for absence in the list obtained by the 2 remaining negative controls (mGluR1, GluR1).

Culturing and Immunoblotting

HEK293T en HeLa cells were grown in DMEM:HAMF10 (1:1) medium containing 10% FBS and 1% penicillin/streptomycin at 37° C. and 5% $CO_2$. Cells were transiently transfected with various DNA constructs using Polyethylenimin (Polyscience, Eppelheim, Germany) and grown for 24 hours after transfection. For glycosylation experiments, cells were treated with Tunicamycin (20 ug/ml, Merck Chemicals) for 24 hours prior to immunoblotting.

For immunoblotting cells were harvested in phosphate buffered saline (PBS) and lysed for 15 minutes at 4° C. in 1% Triton, 20 mM Tris pH7.5, 150 mM NaCl supplemented with complete protease inhibitors (Roche, Woerden, Netherlands). After a 15 seconds sonification step, samples were spun for 5 minutes at 13.000 rpm at 4° C. The supernatant was diluted in 2× Sample buffer (8% SDS/25% Glycerol/0.05M Tris pH 6.8/200 mM DTT/Bromophenol Blue/$H_2O$) and separated on 8 or 10% SDS-PAGE gels, followed by blotting onto PVDF membranes (Biorad, Veenendaal, Netherlands). Blots were blocked with either 2% BSA/0.05% TWEEN®(polysorbate)/PBS (commercial antibodies) or with 0.05% TWEEN®/skimmed milk (patient sera) and incubated overnight at 4° C. with the appropriate antibody. Blots were washed with 0.05% TWEEN®/PBS or 0.05% TWEEN®/skimmed milk for 3 times 5 minutes each at room temperature and incubated with the appropriate secondary antibody. After washing 3 times in 0.05% TWEEN®/PBS and once in PBS, blots were developed with Enhanced Chemiluminescent Western Blotting Substrate (Pierce, Etten-Leur, Netherlands).

Immunocytochemistry

For immunocytochemistry, HeLa cells were grown on Lab-tek chamber slides (Nunc, Uden, Netherlands) and fixed with 4% PFA for 10 minutes, followed by 3 washes of 5 minutes each with PBS and 1 wash of 5 minutes with PBS+ (0.5% Protifar (Nutricia, Zoetermeer, Netherlands), 0.15% glycin, 0.05% Triton in PBS). Cells were stained with the primary antibody (2 hours at room temperature) in PBS+, washed 3 times in PBS and subsequently incubated with secondary antibodies in PBS+ for 1 hour at room temperature. After 3 subsequent washes in PBS slides were mounted in Vectashield (Vector Laboratories, Peterborough, UK) and studied on a DMRBE microscope (Leica, Rijswijk, Netherlands).

For surface staining of DNER, hippocampal neurons were incubated with serum of Tr9 diluted 1:50 and rabbit anti-HA diluted 1:100, in Neurobasal medium (NB) for 15 minutes at 37° C., followed by rinsing in NB at 37° C. After fixing the cells for 10 minutes in 4% PFA/4% sucrose cells were washed three times with PBS, followed by incubation with secondary antibodies in GDB (0.1% gelatin, 16.7 mM Phosphate buffer and 450 mM NaCl) for 1 hour at room temperature. After three subsequent washes in PBS the cover slips were mounted and studied as described above. Permeabilised staining of hippocampal neurons was performed by fixing the neurons in 4% PFA/4% sucrose, 3 washes with PBS and incubation of the primary antibodies in GDB+ 0.6% Triton, overnight at 4° C. After three washes with PBS, neurons were incubated with secondary antibodies for 1 hour at room temperature in GDB+ 0.6% Triton. Subsequent washing and mounting were as described above.

Immunohistochemistry

Snap frozen rat brain and cerebellar cryosections were stained as described before (Graus, F. et al., supra). Cryosections of 6-8 μm were air-dried and fixed in acetone (4° C.) for 10 minutes. Endogenous peroxidase was blocked with 0.3% $H_2O_2$ in PBS. Slides were treated with 10% goat serum for 30 minutes at room temperature (RT), incubated either 2 hours at RT or overnight at 4° C. with patient serum diluted in blocking serum (1:100 or 1:400), with PBS washes between the different steps. Slides were incubated with biotin conjugated goat anti-human IgG antibodies (1:2000, Vector, Peterborough, UK) in blocking serum for 45 minutes. After incubation with Vectastain Elite ABC complex (Vector Labs, Burlingame, Calif.) for 30 minutes, the reaction was developed with 0.05% diaminobenzidine and 0.01% $H_2O_2$ diluted in PBS with 0.5% Triton X-100 followed by staining with Diaminobenzidine tetrahydrochlorid dihydrate (DAB, Fluka, Zwijndrecht, Netherlands) slides were dehydrated with ethanol series (50-100%) and mounted with Pertex (Klinipath, Duiven, Netherlands). To test whether the different Tr-identified sera recognize a similar epitope, rat cerebellar sections were incubated with undiluted anti-Tr-positive serum for 3 hours at RT, after the initial blocking in goat serum. This was followed by overnight incubation at 4° C. with biotinylated purified IgG (biotinylated using EZ-Link® Sulfo-NHS-LC-Biotinylation Kit (Pierce Biotechnology, Rockford Ill., US), diluted 1:100 in PBS 1% BSA, from a serum which had been used in Tr-blocking experiments described before (Bernal, F. et al., 2003, Neurology 60:230-234). Staining was developed as described above.

Purification of DNER Reacting Antibodies from Tr Serum

BioGFP-DNER was expressed in HEK293T cells for 24 hours, washed with cold PBS and lysed for 15 min on ice in 20 mM HEPES pH7.5, 150 mM KCl, 1% Triton X-100, complete protease inhibitors (Roche, Woerden, Netherlands), followed by 2 times 10 seconds sonification steps. Extracts were spun at 13.000 rpm for 10 minutes after which the supernatant was incubated with preblocked (1% BSA, 0.05% TWEEN® in PBS for 30 minutes) Dynal M280 beads (Invitrogen, Breda, Netherlands) for 1 hour. Beads were washed 5 times with HEPES pH7.5, 600 mM KCl, 0.1% Triton X100 and subsequently incubated for 3 hours with patients sera diluted 1:15 in PBS containing 1% BSA and 0.05% TWEEN® at 4° C. The beads were washed 4 times with 20 mM HEPES pH7.5, 600 mM KCl, 0.1% Triton X100 and antibodies were eluted with 200 mM glycine pH2.8, after which the pH was neutralized using ⅒th volume of 1M Tris, pH8.0. Both depleted serum and the purified antibodies were washed with PBS using Vivaspin sample concentrators (GE Healthcare, Hoevelaken, Netherlands) and stored in PBS containing 1% BSA.7

DNER Knock Down in Hippocampal Neurons

Primary hippocampal cultures were prepared from embryonic day 18 (E18) rat brains9. Cells were plated on coverslips coated with poly-L-lysine (30 µg/ml) and laminin (2 µg/ml) at a density of 75,000/well. Hippocampal cultures were grown in Neurobasal medium (NB) supplemented with B27, 0.5 mM glutamine, 12.5 µM glutamate and penicillin/streptomycin as described in Jaworski et al. (supra). The following shRNA sequences targeting rat DNER were used in this study: shRNA#1 (AAACCCTTGGTCACACTGA) and shRNA#2 (GATTCTGTTGCTAAGTCCA). The complementary oligo's were annealed and inserted into pSUPER. Hippocampal neurons were transfected at 7 days in vitro (DIV) using Lipofectamine 2000 (Invitrogen). DNA (3.6 µg/well) was mixed with 3.3 µl Lipofectamine 2000 in 200 µl NB, incubated for 30 minutes and then added to the neurons in NB at 37° C. in 5% $CO_2$ for 45 min. Next, neurons were washed with NB and transferred in the original medium at 37° C. in 5% $CO_2$ for 4 days. Cells were co-transfected with β-galactosidase to identify the transfected cells.

Results

Identification of DNER as Tr-Antigen by Mass Spectrometry

Figure 1A:
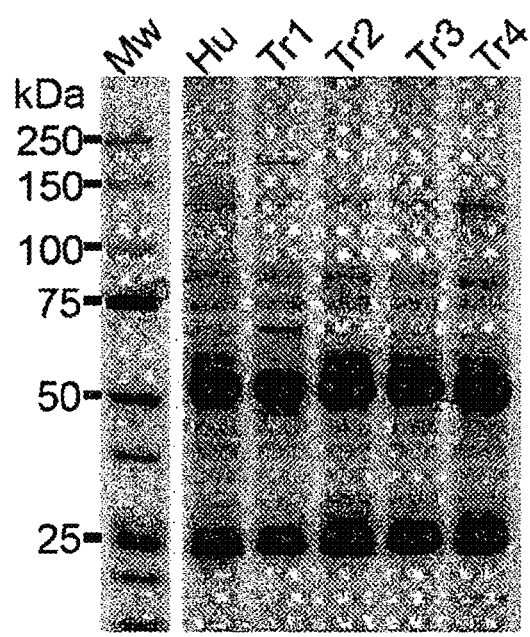
FIGS. 1A-D show identification of DNER as the Tr antigen.

To identify the antigen recognized by Tr-antibodies, we performed immunoprecipitation experiments followed by mass spectrometry on crude rat brain extracts using 4 different anti-Tr positive sera and 3 control sera containing antibodies against Hu, metabotropic glutamate receptor 1 (mGluR1) or glutamate receptor 1 (GluR1). Size fractionation of the purified complexes on SDS-PAGE electrophoresis and subsequent staining with Coomassie blue, showed no apparent protein band shared by all 4 anti-Tr positive sera (FIG. 1A). We nevertheless cut each lane in 15 slices, digested them with trypsin and performed mass spectrometry. The mass spectrometry data of each anti-Tr serum was first analyzed and compared to the results obtained with the Hu, mGluR1 and GluR1 control sera, leaving Delta/notch-like epidermal growth factor (EGF)-related receptor (DNER) as unique protein identified by the anti-Tr sera only, making DNER a good candidate as Tr-antigen.

DNER is the Tr-Antigen in Cell-Based Assay

Figure 1B:
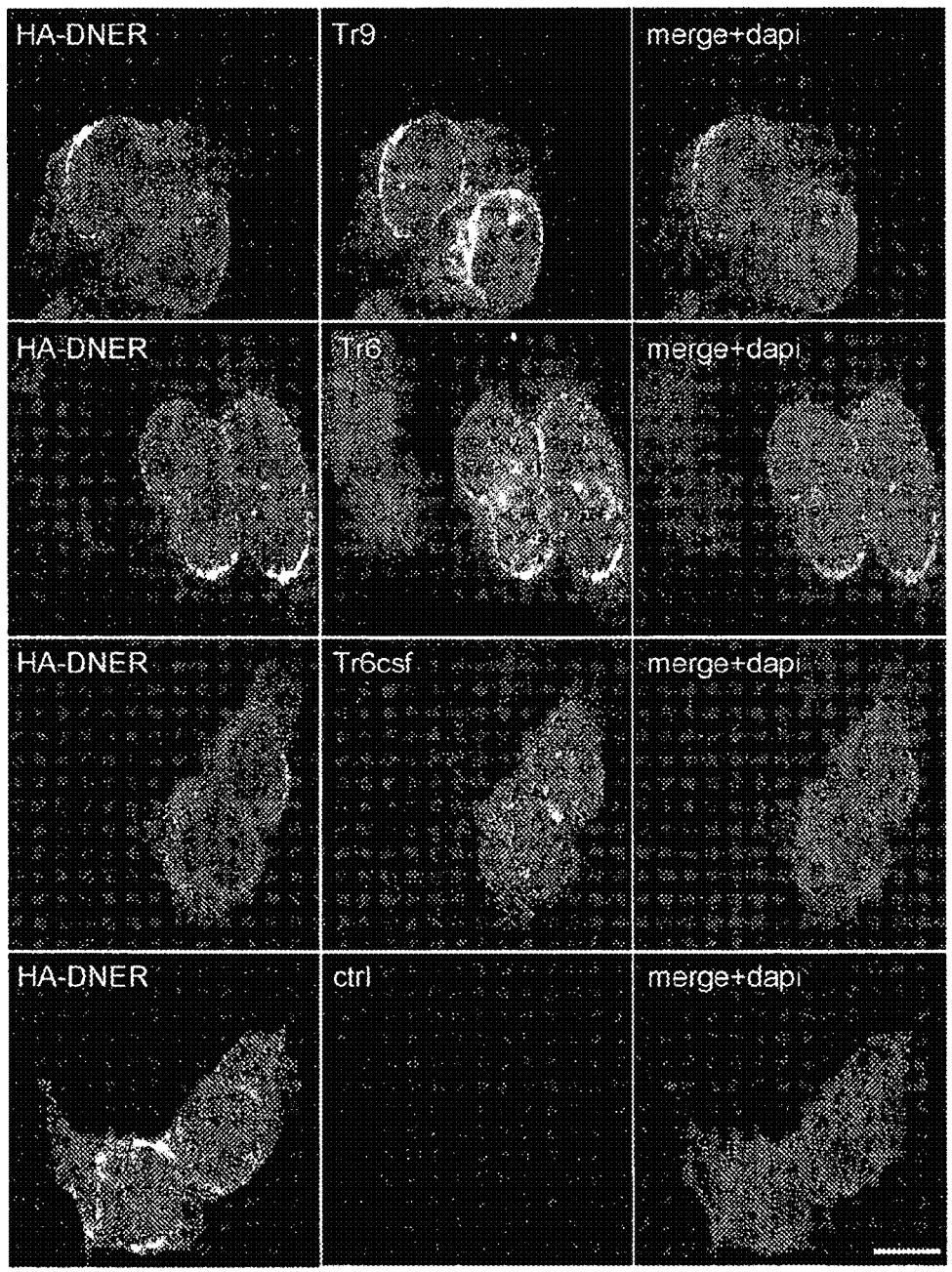
Figure 1C:
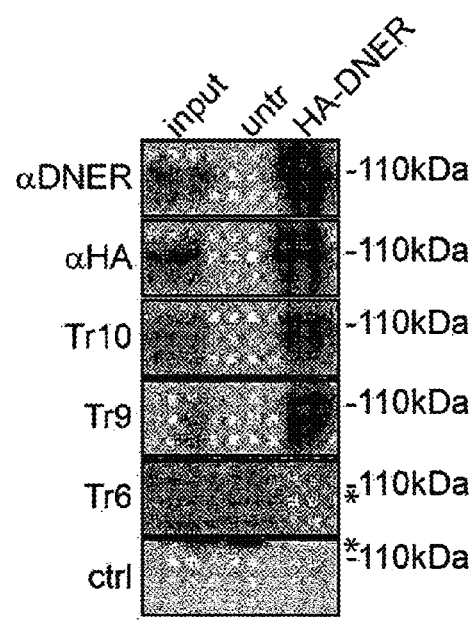
Figure 1D:
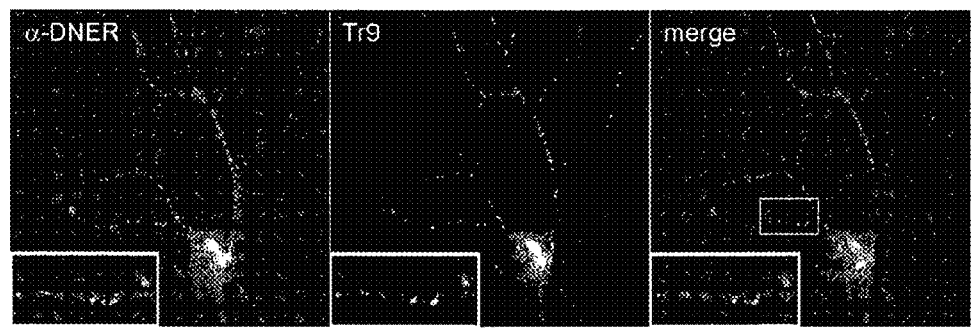

We next performed a cell-based assay to find further evidence for DNER as the Tr-antigen. HeLa cells expressing full length HA-tagged DNER were incubated with anti-HA antibodies and either of two anti-Tr sera, an anti-Tr cerebrospinal fluid (CSF) and a control serum. The two anti-Tr sera and CSF strongly labeled cells expressing HA-DNER, but not untransfected cells (stained with Dapi only, FIG. 1B, top 3 panels). In contrast, the staining was absent in control sera known to detect Hu, mGLUR1 or GluR1 (FIG. 1B, lower panel and data not shown). We next tested all 12 anti-Tr sera as well as 246 control samples (Table 2), using the same cell-based screening assay. All anti-Tr sera positively stained HeLa cells expressing HA-DNER while all but one control samples were negative (FIG. 1B and data not shown). PAGE-7 Interestingly, the one control sample that contained anti-DNER antibodies was from a patient suffering from Hodgkin Lymphoma without any signs of ataxia. Testing this serum on rat brain sections resulted in the characteristic punctate staining typical for Tr (data not shown). As DNER is normally expressed in pyramidal hippocampal neurons, we performed co-staining in primary hippocampal neuron cultures. Under permeabilizing conditions, we detected punctuate somato-dendritic anti-DNER staining of endogenous DNER, which fully co-localizes with Tr-positive sera (FIG. 1D). These results further confirm that DNER is the Tr-antigen.

To determine whether the anti-Tr sera could detect the extracellular domain of DNER, we overexpressed HA-DNER in hippocampal neurons. Surface staining with both anti-HA and anti-Tr sera showed similar reactivity of both antibodies in the somato-dendritic compartment (not shown). This indicates that the DNER epitope is available to the anti-Tr antibodies on the surface of neurons.

DNER is the Tr-Antigen by Western Blot Analysis in Most but not all Anti-Tr Sera Western blot analysis of cerebellar or purified Purkinje cell extracts with anti-Tr sera had so far not identified a common Tr antigen (Graus, F. et al., 1997, supra; Hammack, J. et al., 1992, Neurology 42:1938-1943). Since Western blot analysis is a more commonly used method for detecting autoimmune antibodies (Furneaux, H. M. et al., 1990, N. Engl. J. Med. 322:1844-1851) we tested whether this method could be used for anti-Tr diagnostic purposes. For this, we subjected total HEK293T cell extracts expressing HA-DNER and purified HA-DNER (by anti-HA IP, FIG. 1C) to Western blotting. Of the 12 anti-Tr positive sera tested only three could recognize total input directly (represented by Tr10 FIG. 1C). The other 9 sera were negative (represented by Tr9 in FIG. 1C). Loading the gel with purified HA-DNER, as seen by both anti-HA and anti-DNER antibodies (FIG. 1C) increased the number to 11 positive sera (see Tr9 FIG. 1C). However, serum Tr6, positive for DNER staining in the cell-based assay (FIG. 1B), remained negative (FIG. 1C). We therefore conclude that Western blotting is unreliable for diagnosing anti-Tr antibodies.

DNER Blocks Anti-Tr Antibody Reactivity on Brain Sections

Presence of anti-Tr antibodies is usually diagnosed by strict immunohistochemical criteria of rat frozen cerebellar sections: cytoplasmic labeling of Purkinje cells, combined with a characteristic punctuated somatodendritic staining in the molecular layer (Graus, F. et al., 1998, Acta Neuropathol. 96:1-7) (FIGS. 2A and 2A'). Staining rat brain slices with the commercial antibody against DNER resulted in the identical somatodendritic, punctuate staining of Purkinje cells (FIGS. 2B and 2B'). Both anti-Tr sera and anti-DNER antibodies stained isolated pyramidal neurons in the hippocampus (data not shown), as described before (e.g. Graus et al., 1997, supra). In all 7 cases analyzed with traditional antigen blocking experiments the tested anti-Tr sera abolished the characteristic-staining pattern of the standard anti-Tr serum (FIG. 2C-E).

In addition, we performed cerebellar immunohistochemistry with anti-Tr positive sera from which the anti-DNER antibodies were depleted. Sera incubated with purified biotinylated DNER (DNER-GFP-bio) coupled to streptavidin beads prior to the immunohistochemistry lost their Tr-characteristic staining of Purkinje cells (compare FIG. 2G to F). In contrast, eluted anti-DNER antibodies, showed staining of the Purkinje cells similar to the full serum (compare FIG. 2H to F).

Knock Down of DNER Removes Tr Staining in Hippocampal Neurons

Figure 3A:
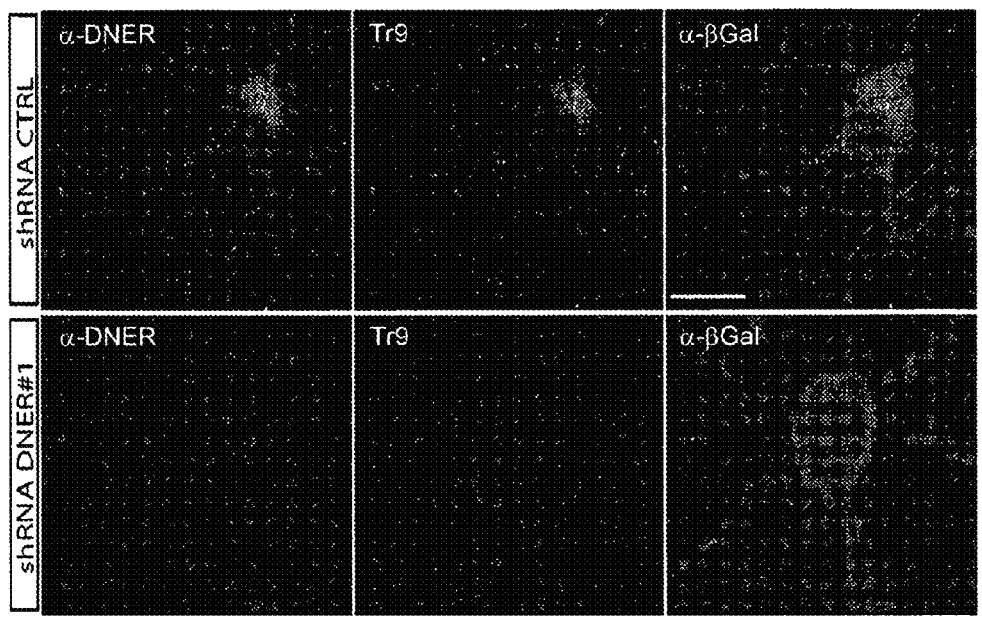
FIGS. 3A-B show knock down of DNER abolishes Tr reactivity in hippocampal neurons.
Figure 3B:
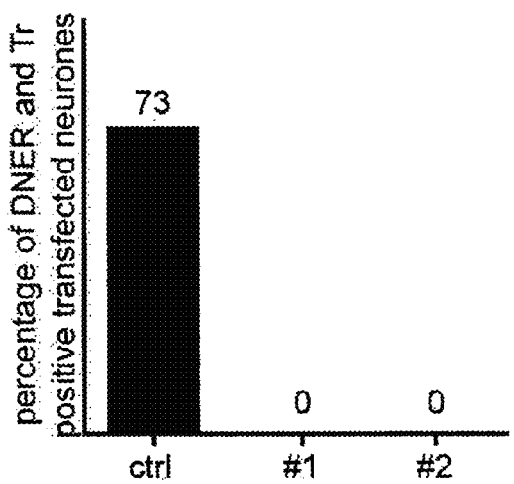

To further demonstrate that DNER is the only protein detected by anti-Tr positive sera we performed DNER knock down experiments. Two independent shRNA-producing constructs directed against DNER were generated and transfected into hippocampal neurons. As endogenous DNER is expressed in pyramidal hippocampal neurons, we counted all transfected neurons as judged by presence of β-Galactosidase and checked for reactivity with anti-DNER and anti-Tr. In control transfections, 73% of the β-Galactosidase expressing neurons (118/162) were positive for both DNER and Tr (FIG. 3A, top panel). In contrast, transfection with two independent shRNA constructs targeting DNER removed both DNER staining, as observed by the commercial anti-DNER antibodies, and Tr staining (Tr9, FIG. 3A, lower panel) in all transfected neurones (133 and 134 neurons respectively for construct 1 and 2, FIG. 3B), further confirming the anti-Tr specificity for DNER.

Mapping of the Tr-Epitope in DNER

Figure 4A:
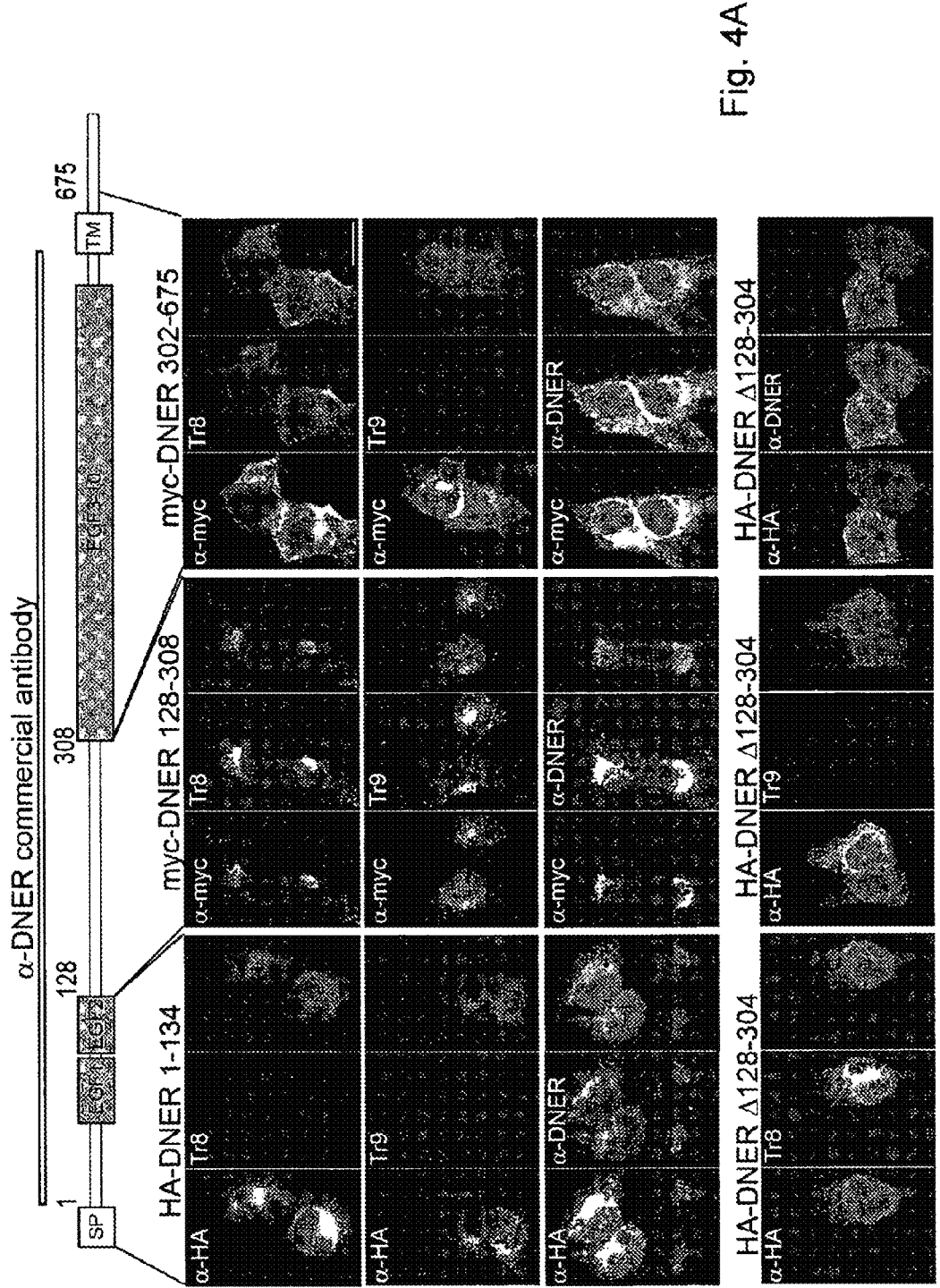
Figure 4E:
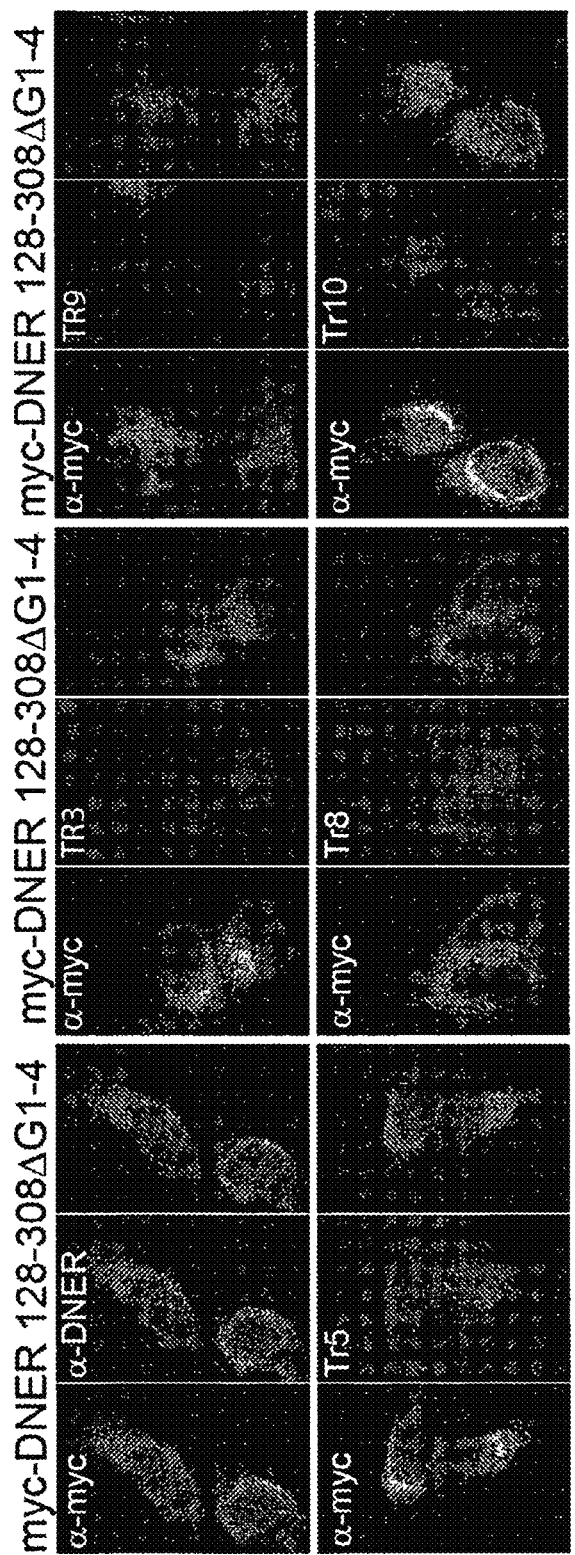

In order to identify the epitope recognized by Tr-positive sera (including the anti-Tr serum from the HL patient without ataxia), we generated different deletion mutants of DNER. We expressed all mutants in HeLa cells and scored whether the different anti-Tr sera reacted with DNER. All anti-Tr sera were found to recognize the extracellular domain of DNER, specifically the region between the second and third EGF-like domain (FIG. 4A, myc-DNER128-308). Interestingly, two different Tr-epitopes are identified within the 13 anti-Tr sera. 7 out of 13 sera recognized only the DNER region between amino acids 128-308 and were negative for the DNER fusion protein lacking this part (represented by Tr9 in FIG. 4A, HA-DNERΔ128-304). In addition, 6 sera recognized a second epitope within the DNER region of amino acid 302-675 and were positive for the DNER fusion protein lacking DNER128-308 (represented by Tr8 in FIG. 4A, myc-DNER302-675 and HA-DNERΔ128-304 respectively). An overview of the epitopes recognized by all 13 different anti-Tr sera using the cell-based assays is given in FIG. 4B. Recognition of the second epitope did not correlate with age, neurological symptoms, underlying type or stage of HL, or functional status of the patients (Table 1).

DNER Glycosylation is Required for Tr Antigenicity

DNER is highly glycosylated (Nishizumi, H. et al., 2002, Neuroreport. 13:909-915). To understand the role of glycosylation in the antigenicity of DNER, we incubated HEK293T cells, expressing HA-DNER without or with glycosylation inhibitor tunicamycin (20 μg/ml, for 24 hr) and analyzed anti-HA immunoprecipitated extracts using Western blot analysis. The removal of glycosylated chains in the majority of DNER protein was confirmed by the reduction in molecular mass of DNER to 90 kDa, close to the expected molecular mass (FIG. 4C). Although non-glycosylated DNER could still be recognized by the commercial anti-DNER antibody (data not shown), both anti-Tr positive sera tested no longer recognized the unglycosylated protein (FIG. 4C). This was confirmed by the lack of staining by anti-Tr sera of Hela cells expressing DNER constructs lacking the N-terminal signal peptide, which block DNER targeting into the endoplasmic reticulum and prevent glycosylation (data not shown). Glycosylation prediction software, NetNGlyc (www.cbs.dtu.dk/services/NetNGlyd) reveals the presence of 4 N-glycosylation sites in the common DNER epitope (amino acids 128-304). We mutated all 4 N-glycosylation sites into alanines (HA-DNERΔG1-4) and analyzed anti-Tr reactivity by immunoprecipitation followed by Western blotting (FIG. 4D). The commercial anti-DNER polyclonal antibodies recognized mutated DNER ΔG1-4, albeit with lower affinity. However, the 2 anti-Tr positive sera tested no longer recognized the mutated DNER (FIG. 4D, Tr9 and Tr10). The role of N-glycosylation for Tr antigenicity was further studied using the cell based assay in which we expressed myc-tagged DNER 128-308ΔG1-4. Two of the anti-Tr sera still recognize mutated DNER, but only very weakly (FIG. 4E, Tr5 and Tr8), whereas all other sera were negative PAGE-11 (FIGS. 4B and E). This strongly indicates the importance of N-glycosylation in recognition of the main DNER epitope by anti-Tr sera.

Applicants incorporate by reference the material contained in the accompanying computer readable Sequence Listing identified as P97562PC00_seqlist_ST25.txt, having a file creation date of Aug. 28, 2014, 10:31 a.m., and a file size of 10.5 kilobytes.

TABLE 1

Characteristics of 11 anti-Tr positive patients. All patients suffered severe cerebellar truncal and limb ataxia with nystagmus and/or cerebellar dysarthria

| Pt No | Sex | Age | Anti-Tr serum titer | MRI | Time from onset to tumor detection (mo) | Tumor | HL subtype | Ann Arbor HL Stage | Tumor treatment | Tumor response | Immunotherapy | mRS worst | mRS end |
|---|---|---|---|---|---|---|---|---|---|---|---|---|---|
| 1 | M | 73 | 6400 | Normal | 4.1 | HL | NS | IIB | ABVD, RT | SD | PE | 3 | 3 |
| 2 | M | 71 | 400 | Normal | 2.9 | HL | NS | IA | VAPEC-B | CR | — | 4 | 4 |
| 3 | M | 50 | 1600 | Normal | 4.3 | HL | NS | IA | EBVP | CR | PE, steroids | 4 | 4 |
| 4 | F | 65 | >400 | WML | — | No tumor | — | — | — | — | — | 5 | 6 |
| 6 | F | 55 | >400 | Old hemorrhage | 7.8 | HL | MC | IIIA | ABVD | CR | PE, IVIG | 5 | 4 |
| 7 | M | 36 | 1600 | Normal | 0.5 | HL | NS | IIA | MOPP/ABV, RT | CR | — | 2 | 2 |
| 8 | M | 29 | 1600 | Normal | 1.0 | HL | NS | IIIB | MOPP/ABV | CR | — | 3 | 0 |
| 9 | M | 35 | 3200 | Normal | 4.8 | HL | NS | IIB | EBVP, RT | CR | PE | 4 | 4 |
| 10 | F | 22 | 6400 | Normal | 4.6 | HL | NS | IIA | ABVD, RT | CR | — | 3 | 2 |

TABLE 1-continued

Characteristics of 11 anti-Tr positive patients. All patients suffered severe cerebellar truncal and limb ataxia with nystagmus and/or cerebellar dysarthria

| Pt No | Sex | Age | Anti-Tr serum titer | MRI | Time from onset to tumor detection (mo) | Tumor | HL subtype | Ann Arbor HL Stage | Tumor treatment | Tumor response | Immunotherapy | mRS worst | mRS end |
|---|---|---|---|---|---|---|---|---|---|---|---|---|---|
| 11 | M | 54 | >400 | Cerebellar atrophy | 10.7 | HL | NS | IIB | MOPP/ABV | CR | — | 2 | 2 |
| 12 | F | 12 | >400 | Normal | 2.1 | HL | NS | IIA | OEPA | CR | IVIG | 4 | 3 |

MRI: WML, white matter lesions; Gd-enhancement, Gadolineum-enhancement; HL, Hodgkin Lymphoma;
HL subtype: NS, nodular sclerosing; MC, mixed cellularity; mRS, modified Rankin Score;
Tumor treatment: ABVD, adriamycin, bleomycin. vinblastine, dacarbazine; RT, radiotherapy; VAPEC-B, vincristine, adriamycin, prednisone, etoposide, cyclophosphamide, bleomycin; EBVP, epirubicin, bleomycin, vinblastine, prednisone; MOPP/ABV, mechlorethamine, Oncovin (vincristine), procarbazine, prednisone/adriamycin, bleomycin, vinblastine; OEPA, Oncovin (vincristine), etoposide, prednisone, adriamycin;
Tumor response: SD = stable disease, PD = progressive disease CR = complete response;
Immunotherapy: PE, plasma exchange; IVIG, intravenous immunoglobulins.

TABLE 2

Control samples

| Sample | n |
|---|---|
| Blood bank controls | 31 |
| Hodgkin Lymphoma without ataxia | 55 |
| Hodgkin Lymphoma with paraneoplastic cerebellar ataxia | 10 |
| Non-Hodgkin Lymphoma without ataxia | 14 |
| Non-Hodgkin Lymphoma with paraneoplastic cerebellar ataxia | 9 |
| Ideopathic cerebellar ataxia | 17 |
| Other autoimmune disease: | |
| SLE | 10 |
| Rheumatoid arthritis | 20 |
| Paraneoplastic cerebellar degeneration with known antibodies: | |
| anti-Yo | 20 |
| anti-Ri | 10 |
| anti-Hu | 20 |
| anti-Ma | 10 |
| anti-Amphiphysin | 10 |
| anti-CV2 | 10 |
| Total | 246 |

The invention claimed is:

1. A method for determining the presence of anti-Tr antibodies in a subject comprising the steps of
   (a) obtaining a sample from said subject, and
   (b) testing for the presence of said antibodies in said sample by addition of glycosylated delta/notch-like epidermal growth factor related receptor (DNER) protein or an antigenic part thereof and checking whether said DNER protein or antigenic part thereof is bound by any anti-Tr antibodies in said sample.

2. The method according to claim 1, wherein the DNER protein or antigenic part thereof is labeled.

3. The method according to claim 1, wherein the sample is a blood, plasma, serum or cerebrospinal fluid (CSF) sample.

4. The method according to claim 1, wherein the method is an immunoassay.

5. The method according to claim 1, wherein the subject is a human subject.

6. The method of claim 1 wherein detection of said DNER protein or antigenic part thereof bound to said Anti-Tr antibodies is correlated with the presence of Hodgkin lymphoma.

7. The method of claim 1 further comprising typing subjects suffering from paraneoplastic cerebellar degeneration and/or ataxia based on detection of said DNER protein or antigenic part thereof bound to said Anti-Tr antibodies.

8. The method of claim 1 wherein a cell line transfected with a construct encoding the DNER protein or antigenic part thereof detects anti-Tr antibodies.

9. A kit for an immunoassay comprising
   (a) a glycosylated delta/notch-like epidermal growth factor related receptor (DNER) protein or antigenic part thereof; and
   (b) an anti-Tr antibody as positive control.

10. The kit according to claim 9, wherein the DNER protein or antigenic part thereof is labeled.

11. The method according to claim 4, wherein the immunoassay is a cell-based immunoassay.

12. The method according to claim 5, wherein the human subject is suffering from paraneoplastic cerebellar degeneration and/or ataxia.

* * * * *